United States Patent [19]

Konishi et al.

[11] Patent Number: 5,002,959
[45] Date of Patent: Mar. 26, 1991

[54] BU-4146T ANTIBIOTIC

[75] Inventors: Masataka Konishi, Kawasaki; Koko Sugawara, Saitama; Masaru Ohbayashi, Tokyo; Takeo Miyaki, Yokohama, all of Japan

[73] Assignee: Bristol-Myers Squibb Company, New York, N.Y.

[21] Appl. No.: 448,441

[22] Filed: Dec. 11, 1989

[51] Int. Cl.$^5$ .................. C07D 405/06; A61K 31/445
[52] U.S. Cl. .................................... 514/326; 546/207; 435/118; 435/253.5
[58] Field of Search .......................... 546/207; 514/326

[56] References Cited

PUBLICATIONS

Frohardt et al., "J. Am. Chem. Soc.", vol. 81, pp. 5500–5506 (1959).
Antibiot, and Chemother. 10: 9–16, 1960.
J. Am. Chem. Soc. 82: 5500–5506, 1959.
J. Anhtibiotics 27 (3): 206–214, 1974.

Primary Examiner—Robert T. Bond
Attorney, Agent, or Firm—David M. Morse

[57] ABSTRACT

A novel antibiotic designated BU-4146T is produced by fermentation of Streptomyces amphibiosporus strain R310-104 (ATCC-53964). The antibiotic possesses both antifungal and antitumor activity.

3 Claims, 1 Drawing Sheet

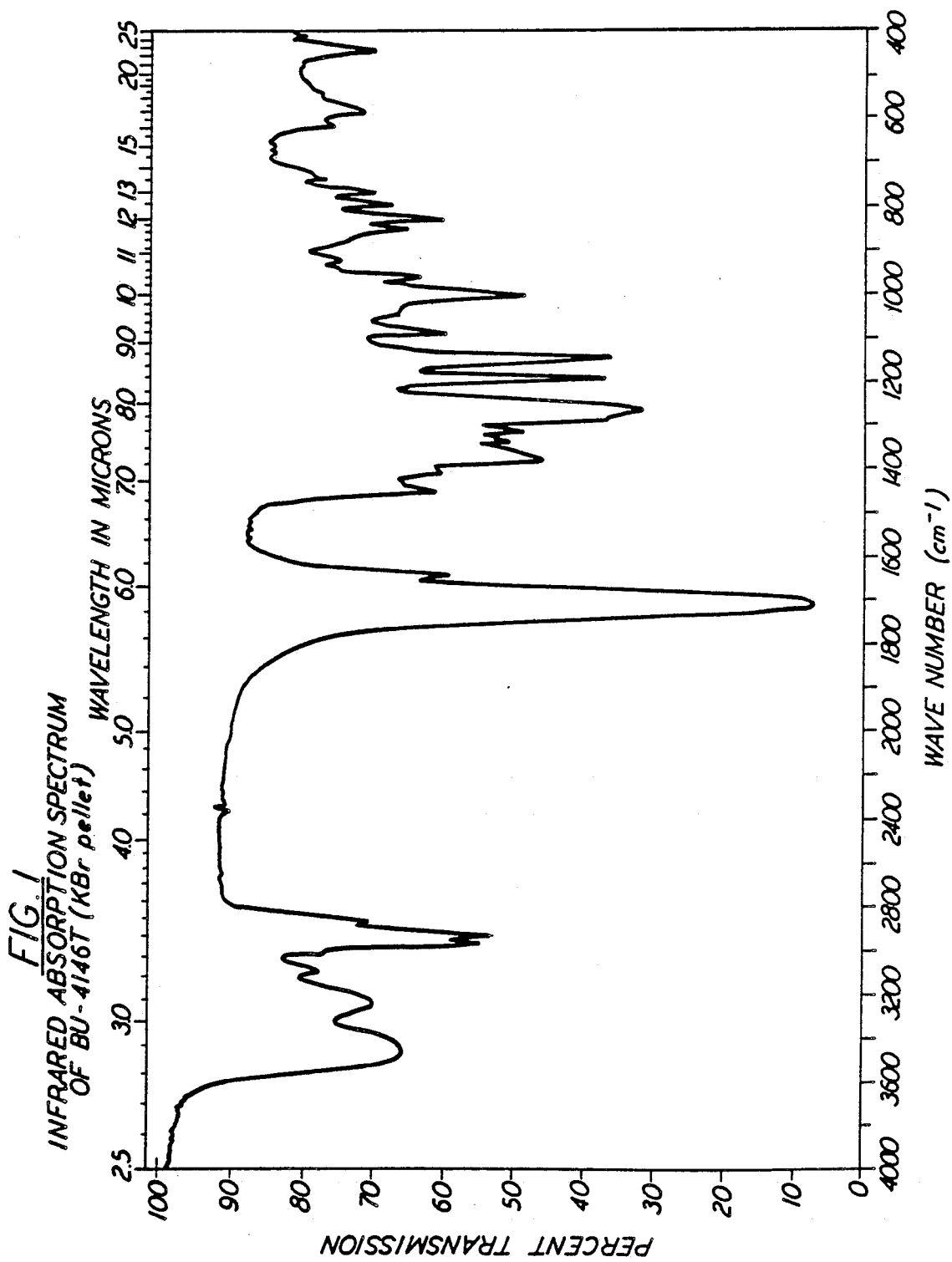

BU-4146T ANTIBIOTIC

BACKGROUND OF THE INVENTION

1. Field of the Invention

This invention is directed to a new antibiotic designated BU-4146T and to a process for the microbiological preparation, isolation and purification of BU-4146T in substantially pure form. BU-4146T is useful as an antifungal and antitumor agent.

2. Description of the Prior Art

The BU-4146T antibiotic of the present invention is a novel member of the glutarimide group of antibiotics. Spectral studies indicate it is composed of a 1-hydroxy-2-(3-glutarimidyl)ethyl group and an unsaturated 12-membered lactone ring.

Among the glutarimide antibiotics, BU-4146T is structurally similar to streptimidone (protomycin) and 9-methylstreptimidone which have an acyclic unsaturated ketone side chain.

Streptimidone has the structure

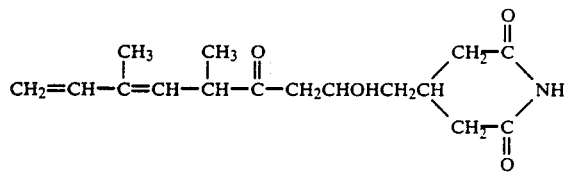

and is disclosed in *Antibiot. and Chemother.* 10: 9–16, 1960 and *J. Am. Chem. Soc.* 82: 5500–5506, 1959.

9-Methylstreptimidone has the structure

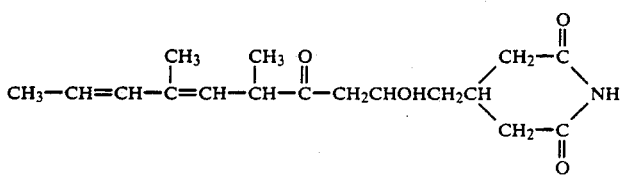

and is disclosed in *J. Antibiotics* 27 (3): 206–214, 1974.

BU-4146T is clearly differentiated from the abovedescribed glutarimide antibiotics by its unique 12-membered lactone side chain and its strong antitumor activity.

BRIEF DESCRIPTION OF THE DRAWINGS

FIG. 1 represents the infrared absorption spectrum of BU-4146T (KBr pellet).

SUMMARY OF THE INVENTION

This invention relates to a novel antibiotic designated BU-4146T and to a fermentation process for preparation of BU-4146T using a new actinomycete designated herein as *Streptomyces amphibiosporus* strain R310-104 (ATCC-53964). The invention also relates to the new microorganism used in the fermentative production of BU-4146T, use of BU-4146T as an antitumor and antifungal agent and pharmaceutical compositions of BU-4146T adapted for antitumor or antifungal use.

DETAILED DESCRIPTION OF THE INVENTION

The Microorganism

BU-4146T may be produced by fermentation of *Streptomyces amphibiosporus* strain R310-104 or a BU-4146T-producing variant or mutant thereof.

The preferred producing strain designated R310-104 was isolated from a soil sample collected in Akita City, Japan.

The cultural and physiological characteristics of strain R310-104 were examined by the methods of Shirling and Gottlieb (*Int. J. Syst. Bacteriol.* 16: 313–340, 1966) and Gordon, et al. (*J.Gen. Microbiol.* 109: 69–78, 1978). Diagnostic components (amino acid and sugar) in the whole cell and the purified cell wall were analyzed by the methods of Lechevalier (*J.Lab.Clin.Med.* 71: 934–944, 1968) and Becker, et al. (*Appl. Microbiol.* 13: 236–243, 1965), respectively. The phospholipids were identified by the methods of Lechevalier, et al. (*Biochem.Syst. Ecol.* 5:249–260, 1977). The menaquinone samples were prepared by the procedures of Collins, et al. (*J.Gen. Microbiol.* 100: 221–230, 1977), and analyzed with a mass spectrometer. The glycolate test and the detection of mycolate were carried out by the methods of Uchida and Aida (*J.Gen.Appl. Microbiol.* 25: 169–183, 1979) and Minnikin, et al. (*J.Gen. Microbiol.* 88: 200–204, 1975), respectively.

Results

Morphology: Substrate and aerial mycelia are long, well-branched and not fragmented into rod or coccoid cells. Both the substrate and aerial mycelia form hook, loop or long spiral hyphae. These curved hyphae in the aerial and substrate mycelia bear chains of spores continuously or intermittently, and the spore chains contain 5 to 50 spores per chain. These spores are spherical or oval (0.6–0.8×0.7–1.2 μm), non-motile and have a smooth surface. Sclerotic granules are occasionally observed. Sporangia and whorl are not formed.

Cultural and physiological characteristics: The growth is moderate on diagnostic media except for poor growth on Czapek's sucrose-nitrate agar. The aerial mycelium, when formed in the mass, is white. The substrate mycelium is yellowish to olive brown. Brownish diffusible pigments are produced in the organic media and tyrosine agar, but the tyrosinase reaction is negative (Tables 1 and 2).

Occurrence of spontaneous mutant: The original culture of strain R310-104 included mutants which lost the ability to form aerial mycelium. A mutant strain No. 101 produced almost the same level of antibiotic BU-4146T as strain R310-104, and was differentiated from strain R310-104 by its moderate growth in Czapek's sucrose-nitrate agar, its maximal tolerance to NaCl at 6%, and its acid formation from L-arabinose and lactose. The mutant was not differentiated from strain R310-104 in terms of the cell chemistry. A biologically pure culture of this mutant strain, designated *Streptomyces amphibiosporus* strain R310-104-101, was deposited with the American Type Culture Collection, Rockville, Md., under accession number ATCC-53965.

Cell chemistry: The whole cell hydrolyzate contains LL-diaminopimelic acid, galactose, madurose and ribose as the main components, and small amounts of mannose and glucose. Purified cell wall contains LL-diaminopimelic acid, glycine, glutamic acid, alanine, and small amounts of aspartic acid, and no neutral sugars. The phospholipids contain phosphatidylethanolamine, phosphatidylglycerol and phosphatidylinositol. Therefore, strain R310-104 belongs to cell wall Type I, sugar pattern B, and phospholipid Type P-II. The predominant menaquinone present is MK-9 ($H_8$). Mycolate is not contained. The glycolate test is negative.

Taxonomic position of strain R310-104: The following characteristics of strain R310-104 are common to the strain and Streptomyces: 1. Spore-chain morphology in the aerial mycelium, 2. Purified cell wall: Type I (containing LL-diaminopimelic acid, glycine and not neutral sugars), 3. Phospholipid pattern P-II containing phosphatidylethanolamine, and 4. The major menaquinone: MK-9 ($H_8$). On the other hand, strain R310-104 can be differentiated from Streptomyces in the following characteristics: 1. Formation of hook or spiral substrate hyphae which partially sporulate in chain and 2. Whole cell hydrolysate: Sugar Pattern B (containing large amounts of madurose and galactose).

TABLE 1

| Cultural characteristics of strain R310-104 | | | | |
| --- | --- | --- | --- | --- |
| Medium | Growth | Aerial mycelium | Substrate mycelium | Diffuseable pigment |
| Sucrose-nitrate agar (Czapek-Dox agar) | Scant | No or very scant | Colorless | None |
| Tryptone-yeast extract broth (ISP No. 1) | Moderate, Not turbid | None | Colorless | None |
| Yeast extract-malt extract agar (ISP No. 2) | Moderate | Poor; white | Deep yellowish brown (75) | Deep yellowish brown (75) |
| Oatmeal agar (ISP No. 3) | Poor | Scant; white | Colorless to light yellow | None |
| Inorganic salts-starch agar (ISP No. 4) | Moderate | Moderate; white | Grayish yellow (90) | None |
| Glycerol-asparagine agar (ISP No. 5) | Moderate | Scant; white | Dark grayish Yellow (91) | Grayish yellow (90) |
| Peptone-yeast extract-iron agar (ISP No. 6) | Moderate | None | Colorless | None |
| Tyrosine agar (ISP No. 7) | Moderate | Poor; white | Dark olive brown (96) | Dark grayish yellowish brown (81) |
| Glucose-asparagine agar | Poor | None | Colorless | None |
| Bennett's agar | Good | Scant; white | Moderate olive brown (95) | Moderate olive brown (95) |

Observation after incubation at 28° C. for 3 weeks. Color name, used: ISCC-NBS color-name charts.

TABLE 2

| Physiological characteristics of strain R310-104 | |
| --- | --- |
| Utilization of: | Growth and acid production |
| Decomposition of: | |
| Adenine | − |
| Hippuric Acid | − |
| Hypoxanthine | + |
| Testosterone | +(w)* |
| Tyrosine | + |
| Xanthine | + |
| Decarboxylation of: | |
| Benzoate | − |
| Citrate | + |
| Malate | + |
| Mucate | − |
| Oxalate | + |
| Succinate | + |
| Tartrate | − |
| Production of: | |
| Amylase | + |
| Esculinase | + |
| Gelatinase | + |
| Nitrate reductase | +/−** |
| Tyrosinase | − |
| Urease | − |
| Growth in: | |
| Lysozyme, 0.01% | − |
| NaCl, 1–10% | + |
| NaCl, 1–12% | − |
| pH 5.0–10.5 | + |
| 19° C.–39° C. | + |
| 15° C. and 41° C. | − |

TABLE 2-continued

| Physiological characteristics of strain R310-104 | |
| --- | --- |
| Utilization of: | Growth and acid production |
| Adonitol | + |
| D-Arabinose | + |
| L-Arabinose | − |
| Cellobiose | − |
| Cellulose | − |
| Dextrin | + |
| Dulcitol | − |
| Erythritol | + |
| D-Fructose | + |
| D-Galactose | + |
| D-Glucose | + |
| Glycerol | + |
| Inositol | + |
| Lactose | − |
| Maltose | + |
| D-Mannitol | + |
| D-Mannose | + |
| D-Melezitose | − |
| Melibiose | − |
| Methyl-α-glucoside | − |
| Raffinose | − |
| L-Rhamnose | + |
| D-Ribose | + |
| Salicin | − |
| Soluble starch | + |
| D-Sorbitol | − |
| L-Sorbose | − |
| Sucrose | + |
| Trehalose | + |
| D-Xylose | + |

*+(w), weakly positive
**+/−, positive in inorganic nitrate broth, and negative in organic nitrate broth

TABLE 3

| Comparisons of strain R310-104 to relevant genera | | | | | | | | | |
| --- | --- | --- | --- | --- | --- | --- | --- | --- | --- |
| | Spore chain | | DAP | | Whole cell | | | | Phospho- |
| | AM | SM | LL | Meso | Mad | Gal | Ara | Xyl | lipid | Menaquinone |
| Strain R310-104 | + | + | + | − | + | + | − | − | PII | MK-9($H_8$) |
| Streptomyces | + | − | + | − | − | v | − | − | PII | MK-9($H_6,H_8$) |
| Actinomadura | + | − | − | + | + | v | − | − | PI/PIV | MK-9($H_6$, $H_8$)/MK-9($H_4$) |
| Kitasatosporia | + | + | + | + | − | + | − | − | PII | MK-9($H_6,H_8$) |
| Nacardiopsis | + | − | − | + | − | − | − | − | PIII | MK-10($H_4,H_6$) |
| Saccharothrix | + | + | − | + | − | + | − | − | PII | MK-9($H_4$),MK-10($H_4$) |
| Glycomyces | + | − | − | + | − | − | + | + | PI | MK-10($H_2,H_6$) |

TABLE 3-continued

| | Spore chain | | DAP | | Whole cell | | | | Phospholipid | Menaquinone |
|---|---|---|---|---|---|---|---|---|---|---|
| | AM | SM | LL | Meso | Mad | Gal | Ara | Xyl | | |
| Excellospora | + | + | − | + | + | − | − | − | PI | MK-9(H$_8$) |

Abbreviations
AM: aerial mycelium, SM: substrate mycelium, DAP: 2,6-diaminopimelic acid, LL: LL-isomer, Meso: meso-isomer, Mad: madurose, Gal: galactose, Ara: arabinose, Xyl: xylose, v: variable (+ or −)

The above-described characteristics of strain R310-104 indicate that the strain is a heretofore undescribed species of actinomycetes. The strain R310-104 has been designated *Streptomyces amphibiosporus*. A biologically pure culture of strain R310-104 has been deposited with the American Type Culture Collection, Rockville, Md., as strain ATCC-53964.

It is to be understood that the present invention is not limited to use of the particular strain described above or to organisms fully answering its description. It is especially intended to include other BU-4146T-producing variants or mutants of the described organism which can be produced by conventional means such as x-radiation, ultraviolet radiation, treatment with nitrogen mustards, phage exposure, and the like.

Antibiotic Production

BU-4146T may be produced by cultivating *Streptomyces amphibiosporus* strain R310-104 (ATCC-53964) or a BU-4146T-producing variant or mutant thereof under submerged aerobic conditions in an aqueous nutrient medium. The organism is grown in a nutrient medium containing an assimilable carbon source, for example, D-arabinose, dextrin, fructose, galactose, glucose, trehalose and soluble starch. The nutrient medium should also contain an assimilable nitrogen source such as fish meal, peptone, soybean flour, peanut meal, cottonseed meal, corn steep liquor, yeast extract or ammonium salts. Inorganic salts such as sodium chloride, potassium chloride, magnesium sulfate, calcium carbonate, phosphates, etc. are added if necessary. Trace elements such as copper, manganese, iron, zinc, etc. are added to the medium if desired, or they may be supplied as impurities of other constituents of the media.

Production of BU-4146T may be effected at any temperature conducive to satisfactory growth of the producing organism, e.g. 19° C.-39° C., but it is preferred to conduct the fermentation at 25°-35° C., most preferably 27°-32° C. Production of the antibiotic is carried out generally for a period of about 4-7 days.

The fermentation may be carried out in flasks or in laboratory or industrial fermentors of various capacities. When tank fermentation is to be used, it is desirable to produce a vegetative inoculum in a nutrient or soil culture or a lyophilized culture of the organism. After obtaining an active inoculum in this manner, it is transferred aseptically to the fermentation tank medium for large scale production of BU-4146T. The medium in which the vegetative inoculum is produced can be the same as, or different from, that utilized in the tank as long as it is such that a good growth of the producing organism is obtained. Agitation during the fermentation can be provided by a mechanical impeller and conventional antifoam agents such as lard oil or silicon oil can be added if needed.

Production of BU-4146T in the fermentation medium can be readily followed during the course of the fermentation by a biological assay.

Isolation of the BU-4146T antibiotic from the fermentation medium and purification of BU-4146T may be achieved by conventional solvent extraction and chromatographic procedures. A preferred isolation and purification procedure is illustrated in Example 2 below.

Physico-chemical Properties of BU-4146T

BU-4146T was isolated as a pale yellow solid. It is readily soluble in acetonitrile, n-butanol, methanol, ethyl acetate, chloroform and dimethyl sulfoxide, but practically insoluble in n-hexane and water. It gave positive responses to iodine vapor and ammonium molybdate-sulfuric acid (AMS), but negative response to ninhydrin and anthrone reagents. The physico-chemical properties of BU-4146T are summarized in Table 4.

TABLE 4

| Physico-Chemical properties of BU-4146T | |
|---|---|
| Nature | Pale yellow solid |
| M.P. | 121–125° C. |
| $[\alpha]_D^{24.5}$ | −20 ± 1° (C 0.5, DMSO) |

Elemental analysis:
Calcd. for $C_{26}H_{35}NO_6 \cdot 1/4 H_2O$: C 67.58, H 7.74, N 3.03
Found: C 67.47, H 8.06, N 2.87
MS p-SIMS: m/z 458(M+H)$^+$, 480(M+Na)$^+$, 496(M+K)$^+$
N-SIMS: m/z 456(M−H)$^-$
IR $\nu_{max}^{KBr}$ cm$^{-1}$: 3450, 3230, 3100, 2960, 2930, 1700, 1640, 1380 1260, 1190, 1140, 1000
TLC (SiO$_2$, Merck F254):
CH$_2$Cl$_2$-MeOH (95:5) Rf 0.36
EtOAc-n-Hexane (10:1) 0.27

TABLE 5

$^1$H and $^{13}$C-NMR data of BU-4146T

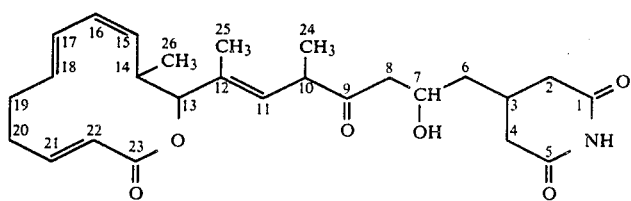

| Carbon No. | $^{13}$C-NMR (100 MHz in DMSO $d_6$) | Protons on Carbon No. | $^1$H-NMR (400 MHz in DMSO $d_6$) |
|---|---|---|---|
| 1 | 173.2(s)$^a$ | 2 | 2.25(m) |
| 2 | 36.9(t)$^b$ |  | 2.50(m) |
| 3 | 26.6(d) | 3 | 2.25(m) |
| 4 | 38.0(t)$^b$ | 4 | 2.25(m) |
| 5 | 173.3(s)$^a$ |  | 2.50(m) |
| 6 | 41.6(t) | 6 | 1.25(m) |
| 7 | 63.7(d) | 7 | 3.96(m) |
| 8 | 48.7(t) | 8 | 2.50(m) |
| 9 | 209.4(s) | 10 | 3.42(dq, 10.4, 6.9) |
| 10 | 45.4(d) | 11 | 5.33(d, 10.4) |
| 11 | 130.0(d) | 13 | 5.24(d, 4.8) |
| 12 | 132.3(s) | 14 | 2.99(ddq, 4.8, 10.9, 6.9) |
| 13 | 82.4(d) | 15 | 5.10(t, 10.9) |
| 14 | 35.5(d) | 16 | 6.04(t, 10.9) |
| 15 | 131.3(d) | 17 | 5.68(dd, 10.9, 15.7) |
| 16 | 128.9(d) | 18 | 5.44(m) |
| 17 | 134.0(d) | 19 | 1.92(m) |
| 18 | 128.1(d) |  | 2.50(m) |
| 19 | 30.6(t) | 20 | 1.92(m) |
| 20 | 31.7(t) |  | 2.50(m) |
| 21 | 147.0(d) | 21 | 6.40(ddd, 5.2, 10.9, 16.1) |
| 22 | 127.6(d) | 22 | 5.51(d, 16.1) |
| 23 | 165.7(s) | 24 | 1.04(d, 6.9) |
| 24 | 15.7(q) | 25 | 1.72(d, 1.2) |
| 25 | 14.6(q) | 26 | 0.86(d, 6.9) |
| 26 | 17.0(q) | —NH | 10.67(s) |
|  |  | —OH | 4.74(d, 5.7) |

$a, b$ assignments may be interchanged

BU-4146T showed only end absorption in the UV spectrum. Its molecular formula was determined to be $C_{26}H_{35}NO_6$ on the basis of microanalysis and mass spectral studies. The IR spectrum in KBr (FIG. 1) showed strong absorption at 3230 and 1700 cm$^{-1}$ suggesting the presence of the imide group. The SIMS spectrum exhibited pseudomolecular ion peaks at m/z 458 (M+H)$^+$, m/z 480 (M+Na)$^+$ and 496 (M+K)$^+$. A strong fragment ion peak at m/z 180 ($C_9H_{10}NO_3$) which is commonly observed for the glutarimide group antibiotics was seen in the EIMS spectrum of BU-4146T. The $^1$H-NMR spectrum (Table 5) (DMSO-$d_6$) exhibited three methyls ($\delta$0.86 d, 1.04 d and 1.72 d), six olefinic protons ($\delta$: 5.10 t, 5.44 m, 5.51 d, 5.68 dd, 6.04 t and 6.40 ddd), one imide proton ($\delta$: 10.67 s) and one hydroxy proton ($\delta$: 4.74 d). The $^{13}$C-NMR (FIG. 3) demonstrated 26 carbons including three methyl, six methylene, five methine, eight olefinic and four carbonyl carbons. The correlation of the protons and carbons was established as shown in Table 2 by $^1$H-$^1$H and $^{13}$C-$^1$H COSY spectra (Table 5) allowed assignment of the following partial structures.

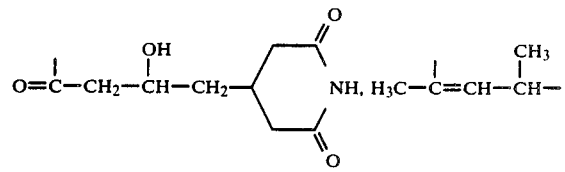

-continued

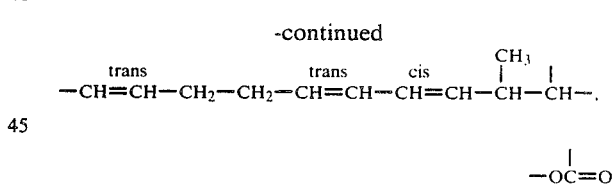

The connection of these fragments was performed by $^{13}$C-$^1$H long range COSY experiments, and the total final structure of BU-4146T was determined to be

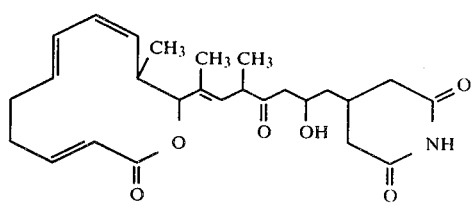

BU-4146T (16 mg) dissolved in methanol (5 ml) was hydrogenated over 20% palladium/charcoal (16 mg) for 16 hours. The catalyst was removed by filtration and the reaction mixture was evaporated in vacuo. The residue was chromatographed on a column of Sephadex LH-20 developing with methanol to yield hexahydro-BU-4146T (10 mg).

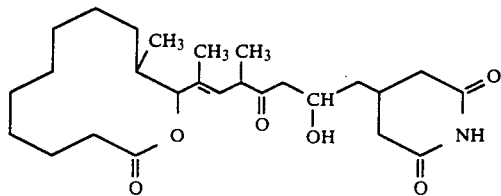

This derivative showed weak cytotoxicity and its activity was about one hundred times weaker than that of BU-4146T. The EIMS spectrum exhibited the molecular ion peak at m/z 463 (M)+ and abundant fragment ion peak at m/z 180 ($C_9H_{10}NO_3$), m/z 265 (M)+—$C_9H_{12}NO_4$) and m/z 308 (M+—$C_7H_{10}NO_3$) supporting the assigned structure of BU-4146T.

Biological Activity

The minimum inhibitory concentrations (MICs) of BU-4146T were determined against various bacteria and fungi by the serial agar dilution method. Nutrient agar (Eiken) was used for bacteria and Sabouraud dextrose agar (Difco) for fungi. The inoculum size was adjusted to $10^2$–$10^4$ cfu/ml for bacteria and $10^3$ cfu/ml for fungi.

BU-4146T did not show inhibitory activity against Gram-positive and Gram-negative bacteria at 100 mcg/ml. As summarized in Table 6, the compound exhibited potent activity against *Cryptococcus neoformans*, *Aspergillus fumigatus*, *Fusarium moniliforme* and *Mucor spinosus*. However, *Candida albicans* and *Trichophyton mentagrophytes* were slightly less sensitive to the antibiotic. As a whole, antifungal activity of BU-4146T was 30–100 times more potent than that of streptimidone, a related glutarimide group antibiotic.

TABLE 6

Antifungal activity of BU-4146T

| Test organisms | | MIC (mcg/ml) | |
|---|---|---|---|
| | | BU-4146T | Streptimidone |
| *Candida albicans* | IAM4888 | >100 | >100 |
| *Candida albicans* | A9540 | >100 | >100 |
| *Cryptococus neoformans* | D49 | 3.1 | 50 |
| *Cryptococus neoformans* | IAM4514 | 3.1 | 50 |
| *Aspergillus fumigatus* | IAM2530 | 0.8 | >100 |
| *Aspergillus fumigatus* | IAM2034 | 1.6 | >100 |
| *Aspergillus flavus* | FA21436 | 3.1 | >100 |
| *Fusarium moniliforme* | A2284 | 0.8 | 50 |
| *Piricularia oryzae* | D91 | 3.1 | >100 |
| *Trichophyton mentagrophytes* | D155 | 100 | >100 |
| *Trichophyton mentagrophytes* | No. 4329 | 100 | >100 |
| *Blastomyces dermatidis* | IF08144 | 12.5 | >100 |
| *Sporothrix schenckii* | IF08158 | 100 | >100 |
| *Petriellidium boydii* | IF08078 | 3.1 | >100 |
| *Mucor spinosus* | IF05317 | 1.6 | >100 |

BU-4146T was tested for in vitro cytotoxicity against murine and human cell lines and for in vivo antitumor activity in mice. Mitomycin C was used as a reference compound in both in vitro and in vivo experiments.

B16-F10 (murine melanoma) and Moser (human colorectal carcinoma) cells were grown to the logarithmic phase in enriched Eagle minimum essential medium supplemented with fetal calf serum (FCS, 10%) and kanamycin (60 mcg/ml), and HCT-116 (human colon carcinoma) cells were grown in Maccoy's 5A medium supplemented with FCS (10%), penicillin (100 U/ml) and steptomycin (100 mcg/ml). B16-F10, Moser and HCT-116 cells were harvested and implanted into wells of 96-well microtiter plate with test materials at the inoculum sizes of $3 \times 10^4$, $6 \times 10^4$ and $6 \times 10^4$ cell/ml, respectively. They were incubated at 37° C. in a humidified atmosphere of 5% carbon dioxide and 95% air for 72 hours. The cytotoxicity against the tumor cells was determined colorimetrically at 540 nm after staining viable cells. The results are summarized in Table 7. BU-4146T was quite active against the above tumor cell lines and the $IC_{50}$ values of the compound were approximately 20–60 times superior to those of mitomycin C.

TABLE 7

In vitro cytotoxicity against murine and human tumor cells.

| | $IC_{50}(\mu g/ml)$ | | |
|---|---|---|---|
| Compound | B16-F10 | Moser | HCT-116 |
| BU-4146T | 0.03 | 0.047 | 0.014 |
| Mitomycin C | 0.50 | 1.2 | 0.80 |

Inhibitory effects of BU-4146T on the macromolecule (DNA, RNA and protein) synthesis were determined in cultured B16-F10 melanoma cells. B16-F10 cells ($10^5$ cells/ml) were incubated with the compound at 37° C. for 3.5 hours (for DNA synthesis) or 4 hours (for RNA and protein synthesis). Labelled presursor, $^3$H-thymidine, $^{14}$C-uridine or $^3$H-leucine was added to the culture and further incubated for 30 minutes (for DNA) or 60 minutes (for RNA and protein). After washing with chilled 5% trichloroacetic acid solution, the radio activity incorporated into the acid-insoluble fraction of the tumor cells was determined by a liquid scintillation counter. As shown in Table 8, BU-4146T inhibited both DNA and protein synthesis to the same extent and the potency was almost 200 times higher than that in RNA synthesis in terms of $IC_{50}$.

TABLE 8

Inhibition of macromolecule synthesis in B16-F10 melanoma cells

| | $IC_{50}(\mu g/ml)$ | | |
|---|---|---|---|
| Compound | DNA | RNA | Protein |
| BU-4146T | 0.023 | 4.2 | 0.024 |
| Mitomycin C | 1.6 | 11 | 60 |

The in vivo activity of BU-4146T was tested in experimental mouse tumor systems. Female $CDF_1$ mice were intraperitoneally inoculated with 0.4 ml of diluted ascitic fluid containing $10^6$ lymphocytic leukemia P388 cells and male $BDF_1$ mice were intraperitoneally inoculated with 0.5 ml of 10% melanotic melanoma B16 brei. Test compounds were intraperitoneally administered to mice by the following treatment schedule; once on day 1 only (QID×1), on days 1, 5 and 9 (Q4D×3) or on days 1 to 9 (QID×9). When administered by the QID×9 schedule in the P388 experiment, BU-4146T was as active as mitomycin C in terms of minimum effective dose (Table 9), whereas it gave moderate activity with maximum T/C of 145% against B16 melanoma (Table 10).

TABLE 9

Antitumor activity by BU-4146T against P388 leukemia (ip)

| Compound | Dose (mg/kg/day) | Treatment schedule (ip) | MST*1 (day) | T/C (%) | Body weight change on day 4 (g) |
|---|---|---|---|---|---|
| BU-4146T | 8 | Q1D × 1 | 8.0 | 73 | −1.5 |
|  | 4 | " | 15.0 | (136)*2 | −1.5 |
|  | 2 | " | 13.0 | 118 | +0.3 |
|  | 1 | " | 12.5 | 114 | +0.8 |
| BU-4146T | 4 | Q4D × 3 | 12.0 | 109 | −1.0 |
|  | 2 | " | 15.0 | (136) | 0.0 |
|  | 1 | " | 15.0 | (136) | +0.8 |
|  | 0.5 | " | 12.0 | 109 | +0.5 |
|  | 0.25 | " | 11.5 | 105 | +0.5 |
| Mitomycin C | 4 | Q4D × 3 | 20.0 | (182) | 0.0 |
|  | 2 | " | 17.0 | (155) | 0.0 |
|  | 1 | " | 15.5 | (141) | +0.8 |
|  | 0.5 | " | 14.5 | (132) | +1.0 |
| Vehicle | — | Q4D × 3 | 11.0 | — | +0.8 |
| BU-4146T | 1 | Q1D × 9 | 14.5 | (145) | +0.5 |
|  | 0.5 | " | 13.5 | (135) | +0.5 |
|  | 0.25 | " | 14.0 | (140) | +0.8 |
|  | 0.13 | " | 12.0 | 120 | 0.8 |
|  | 0.063 | " | 11.0 | 110 | +1.5 |
| Mitomycin C | 1 | Q1D × 9 | 17.0 | (170) | −0.8 |
|  | 0.5 | " | 15.5 | (155) | 0.0 |
|  | 0.25 | " | 13.0 | (130) | +1.0 |
|  | 0.13 | " | 12.0 | 120 | +1.3 |
|  | 0.063 | " | 11.0 | 110 | +0.8 |
| Vehicle | — | Q1D × 9 | 10.0 | — | +0.8 |

*1 Median survival time
*2 Circle indicates significant antitumor effect (T/C ≧ 125%)

TABLE 10

Antitumor activity of BU-4146T against B16 melanoma (ip)

| Compound | Dose (mg/kg/day) | schedule (ip) | MST*1 (day) | T/C (%) | Body weight change on day 4 (g) |
|---|---|---|---|---|---|
| BU-4146T | 4 | Q4D × 3 | 12.5 | 86 | −1.3 |
|  | 2 | " | 21.0 | (145)*2 | +0.8 |
|  | 1 | " | 17.5 | 121 | +0.3 |
|  | 0.5 | " | 17.0 | 117 | +0.3 |
|  | 0.25 | " | 17.0 | 117 | +1.0 |
| Mitomycin C | 2 | Q4D × 3 | 27.5 | (190) | +0.3 |
|  | 1 | " | 20.0 | (138) | +0.8 |
|  | 0.5 | " | 15.0 | 103 | 0.0 |
|  | 0.25 | " | 14.5 | 100 | +0.5 |
| Vehicle | — | Q4D × 3 | 14.5 | — | +0.3 |

*1 Median survival times
*2 Circle indicates significant antitumor effect (T/C ≧ 125%)

As indicated above, BU-4146T exhibits both antifungal and antitumor activities.

In one aspect then, the present invention provides a method of treating an animal host affected by a fungal infection which comprises administering to said host an effective antifungal dose of BU-4146T or a pharmaceutical composition thereof.

In yet another aspect, the present invention provides a pharmaceutical composition comprising an effective antifungal amount of BU-4146T in combination with an inert pharmaceutically carrier or diluent.

According to another aspect of the present invention, there is provided a method of therapeutically treating a mammalian host affected by a malignant tumor sensitive to BU-4146T which comprises administering to said host an effective tumor-inhibiting dose of BU-4146T or a pharmaceutical composition thereof.

Finally, the present invention provides a pharmaceutical composition which comprises an effective tumor-inhibitory amount of BU-4146T in combination with an inert pharmaceutically acceptable carrier or diluent.

The pharmaceutical compositions provided by the present invention may contain other active ingredients, e.g. other antifungal or antitumor agents, and may be made up in any form appropriate for the desired route of administration. Examples of such compositions include solid compositions for oral administration such as capsules, tablets, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or other sterile injectable medium immediately before use.

Optimal dosages and regimens of BU-4146T for a given host can be readily ascertained by those skilled in the art. It will of course be appreciated that the actual dose of BU-4146T used will vary according to the particular composition formulated, the mode of application and particular situs, host and disease being treated. Many factors that modify the action of the drug will be taken into account including age, sex, weight, diet, time of administration, route of administration, rate of excretion, condition of the patient, drug combinations, reaction sensitivities and severity of the disease.

The following specific embodiments are intended to be merely illustrative and not to limit the scope of the invention.

EXAMPLE 1

Fermentation of BU-4146T

A loopful of mature slant culture of *Streptomyces amphibiosporus* strain No. R310-104 (ATCC-53964) was inoculated into a 500-ml Erlenmeyer flask containing 100 ml of seed medium consisting of soluble starch (Nichiden Kagaku) 2%, Pharmamedia (Trader's Protein) 1%, $ZnSO_4.7H_2O$ 0.003% and $CaCO_3$ 0.4% (pH 7.0, before being autoclaved). The seed medium was incubated at 32° C. for 7 days on a rotary shaker (200 rpm) and 5 ml of the resultant culture was transferred into a 500 ml Erlenmeyer flask containing 100 ml of production medium consisting of Protein-S ® (Ajinomoto Co.) 3%, glucose 3%, Pharmamedia 0.5%, yeast extract (Oriental Yeast Co.) 0.1% and $CaCO_3$ 0.3% (pH 7.0, before sterilization). The fermentation was carried out at 28° C. for 7 days on a rotary shaker (200 rpm). Antibiotic production in the fermentation broth was monitored by the in vitro cytotoxic activity against B16 melanoma cells. The activity was observed at ×256 dilution in terms of MED (minimum effective dose) after 4 to 7 days fermentation.

EXAMPLE 2

Isolation and Purification of BU-4146T

The harvested broth (18L, pH 7.4) of *Streptomyces amphibiosporus* strain No. R310-104 obtained according to the procedure of Example 1 was stirred with butanol (18L) for one hour. The solvent layer was separated with a Sharples-type centrifuge and evaporated in vacuo. The residue (30g) was suspended in water (1 L) and extracted three times with 1 L each of ethyl acetate. The combined organic extracts were concentrated to a brown oil which was added dropwise into n-hexane (600 ml) to precipitate a crude solid of BU-4146T (2.65 g). It was applied on a column of silica gel (Wako gel C-200, φ 2.0×50 cm) which was developed with methylene chloride-methanol mixture (ratio from 100:0 to 90:10, v/v). The elution was monitored by antifungal activity against *Cryptococcus neoformans* IAM 4514 using paper disc assay and by cytotoxicity against B16 melanoma cells. The active fractions were combined and evaporated in vacuo to yield a pale yellow solid which was rechromatographed on a column of silica gel (φ 2.0×35 cm) pre-equilibrated with ethyl acetate-n-hexane (1:1, v/v). The elution was performed with the same solvent and the bioactive fractions were pooled and concentrated to dryness. The solid obtained was further purified by Sephadex LH-20 chromatography (φ 2.2×60 cm) using methanol. The active fractions were combined and evaporated in vacuo to afford a pure solid of BU-4146T (45 mg).

We claim:

1. The antibiotic compound designed BU-4146T having the formula.

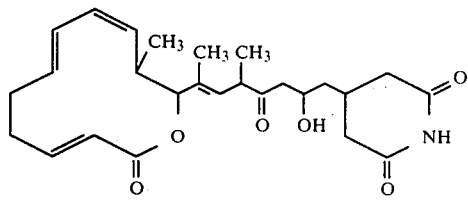

2. A pharmaceutical composition for use in therepeutically treating an animal host affected by a fungal infection comprising a therapeutically effective amount of BU-4146T and a pharmaceutically acceptable carrier or diluent.

3. A pharmaceutical composition for use in therapeutically treating a mammalian host affected by a tumor sensitive to BU-4146T comprising a tumor-inhibiting amount of BU-4146T and a pharmaceutically acceptable carrier or diluent.

* * * * *